United States Patent [19]

Seiler et al.

[11] 4,152,346

[45] May 1, 1979

[54] BETA-AMINOETHYLSILANES AND A METHOD OF PREPARING SAME

[75] Inventors: Claus-Dietrich Seiler, Rheinfelden; Hans-Peter Schwarz, Karsau; Hans-Joachim Kotzsch, Rheinfelden; Hans-Joachim Vahlensteck, Wehr, all of Fed. Rep. of Germany

[73] Assignee: Dynamit Nobel Aktiengesellschaft, Troisdorf, Fed. Rep. of Germany

[21] Appl. No.: 533,728

[22] Filed: Dec. 17, 1974

[30] Foreign Application Priority Data

Dec. 31, 1973 [DE] Fed. Rep. of Germany ....... 2365272

[51] Int. Cl.$^2$ .............................. C07F 7/18; C07F 7/10
[52] U.S. Cl. ..................... 260/448.8 R; 260/448.2 N; 260/448.2 E
[58] Field of Search ............................... 260/448.2 N; 260/448.8 R, 448.2 E

[56] References Cited

U.S. PATENT DOCUMENTS

| | | | |
|---|---|---|---|
| 2,557,803 | 6/1951 | Sommer | 260/448 R UX |
| 2,835,690 | 5/1958 | Prober | 260/448.2 N |
| 2,919,173 | 12/1959 | Roff | 260/448.2 N X |
| 2,955,127 | 10/1960 | Pike | 260/448.8 R X |
| 3,168,389 | 2/1965 | Eilerman | 260/448.2 N X |
| 3,819,672 | 6/1974 | Joslyn | 260/448.2 N |
| 3,823,098 | 7/1974 | Joslyn | 260/448.2 N X |
| 3,837,876 | 9/1974 | Mayuzumi et al. | 260/448.2 N X |
| 3,864,373 | 2/1975 | Seiler et al. | 260/448.8 R |

OTHER PUBLICATIONS

Noll et al., J.A.C.S., 73, p. 3867, 1951.
Noll, "Chemistry and Technology of Silicones", Academic Press, N.Y. (1968), p. 186.
Noll, "Chemistry and Technology of Silicones", Academic Press, N.Y. (1968), p. 174.

Primary Examiner—Paul F. Shaver
Attorney, Agent, or Firm—Sprung, Felfe, Horn, Lynch & Kramer

[57] ABSTRACT

Aminoethylsilanes of the following formula:

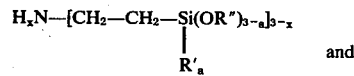

and aminoethylsiloxanes having the structural units

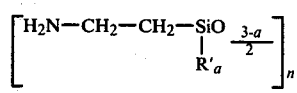

in which R' represents an aliphatic, saturated or unsaturated hydrocarbon group having 1 to 10 carbon atoms, R" represents an alkyl or oxalkyl radical or the phenyl radical, and a can be equal to 0 or 1 and x equal to 0 or 1 or 2; a process for preparing such aminoethylsilane or aminoethylsiloxane which comprises contacting a beta-halogenethylsilane of the formula:

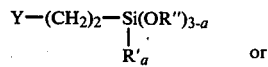

or a siloxane with the recurrent structural unit

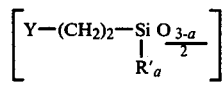

wherein R' is a saturated or unsaturated aliphatic hydrocarbon radical, R" is an alkyl, oxyalkyl or phenyl radical, Y is a halogen atom, a is 0 or 1 and with ammonia at a temperature between 50 and 120° C.

17 Claims, No Drawings

BETA-AMINOETHYLSILANES AND A METHOD OF PREPARING SAME

BACKGROUND OF THE INVENTION

1. Field of the Invention

This invention is directed to beta-aminoethylsilanes and the corresponding organopolysiloxanes in which two methylene groups are present in the repeating unit between the silicon and the amino group. This invention is also directed to a process of preparing these compounds by contacting the corresponding chlorosilane with ammonia.

2. Discussion of the Prior Art

From German patents Nos. 881,654 and 1,023,462 aminoalkylsilanes are known in which there are either one or three methylene groups present between the amino group and the silicon atom. Aminoalkylsilanes having two methylene groups between the amino group and the silicon atom are not disclosed in these patents owing to the fact that these compounds could not be prepared by the processes therein disclosed. In such patents the preparation of aminoalkylsilanes having one or three methylene groups between the silicon atom and the amino group was prepared by reaction of a beta-chloroalkylsilane with ammonia. However, it had been found that beta-chloroethylsilanes could not be employed to prepare beta-aminoethylsilane by reaction with ammonia for beta elimination of the halogen takes place in accordance with known organic chemistry.

According to the known processes, a halogen atom in the beta position is readily cleaved by the action of bases to form the corresponding olefin in accordance with the following equation

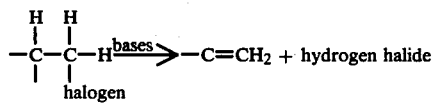

It therefore became desirable to provide a process for the preparation of beta-chloroethylsilanes particularly a process employing ammonia. It also became desirable to provide a process for the preparation of beta-aminosiloxanes having a repeating structural unit wherein there are only two carbon atoms in the linkage between the amino group and the silicon atom.

SUMMARY OF THE INVENTION

In accordance with the present invention a process has been discovered for the preparation of beta-aminosilanes of the formula

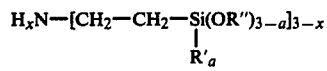

or beta-aminosiloxanes having the repeating structural units

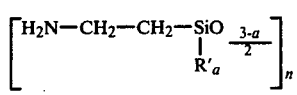

in which R' is an aliphatic, saturated or unsaturated hydrocarbon group having 1 to 10 carbon atoms, R" is an alkyl or hydroxyalkyl or phenyl radical, a is 0 or 1, x is 0, 1 or 2 and n is greater than 2 which comprises contacting a beta-halogenethylsilane of the formula

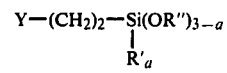

or a siloxane having the repeating structural unit

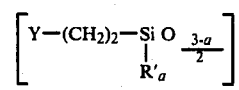

wherein R', R" and a have the previously assigned significance, Y is a halogen atom, with ammonia at a temperature between 50° and 120° C.

In accordance with the present invention it has been surprisingly found that when a beta-chloroethysilane or a corresponding siloxane are reacted with ammonia at a temperature between 50° and 120° C. that beta elimination of the halogen atom does not proceed to a substantial extent and there can be recovered the corresponding beta-aminosilane or siloxane. These beta-aminosilanes or siloxanes are a predominant component in the resulting product.

Thus, the present invention is particularly concerned with the preparation of aminosilanes and aminosiloxanes wherein the reaction of the beta-chloroethylsilane or siloxane is carried out at a temperature between 50° and 120° C. As reactants there are employed compounds having the following formulae

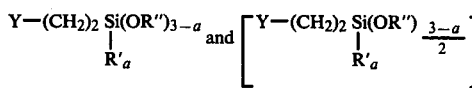

in which R', R" and a have the previously assigned significance. In this formula Y is preferably chlorine although compounds having other halogen atoms can be employed as reactants, notably wherein the Y moiety is, bromine or iodine.

While beta-aminoethylsilanes have broadly been known as disclosed in German Offenlegungsschrift No. 2,161,712 these compounds have been characterized by having one of the hydrogen atoms of the alkylene group disposed between the silicon atom and the amino group substituted by an alkyl group. These aminosilanes were not prepared by the reaction of a corresponding chlorosilane with ammonia, but by the addition of amines having olefinic double bonds to hydrogensilanes in the presence of a platinum compound employed as a catalyst. Thus, at the time of the filing of the German application maturing into this Offenlegungsschrift it was generally conceded by those in the art that the above mentioned beta elimination would prevail predominantly in the reaction of beta-chlorosilanes with ammonia, particularly a beta-chlorosilanes wherein the alkylene group has two carbon atoms between the silicon atom and the chlorine atom.

It has been found, of course, that this beta elimination for some reason does not predominate in the process of the invention. In the herein described invention, beta-chloroethylsilanes are employed as reactants. These reactants are known compounds. They can be prepared either by the reaction of vinyl silanes with hydrochloric acid or by the chlorination of ethyltrichloro silanes. The alkoxy groups of the chlorosilanes are preferably methoxy or ethoxy groups. The process of the invention can, however, be performed in the same manner when the alkoxy group has a greater number of carbon atoms as, for example, where the alkoxy group is a butoxy group or when the carbon chain is interrupted by an ether-oxygen bridge, as for example in β-chloroethyl-tris-(β-methoxyethoxy)-silane or β-chloroethyl-tris-(β-ethoxyethoxy)-silane. Generally speaking, the alkoxy group of the β-chlorethylsiloxane reactants can have between 1 and 8 carbon atoms therein.

In the formulae expressed above, R' refers preferably to a methyl or ethyl radical. Generally speaking, R' is either an alkyl radical having between 1 and 4 carbon atoms in the chain.

Substantially the same teachings apply to the situation wherein the reactant is a chloroethylsiloxane. The values for R' for a chloroethylsiloxane are the same as where the reactant is a chloroethylsilane. These siloxanes can be prepared simply by hydrolyzing the corresponding chlorosilanes by known methods with an amount of water such as is required for the achievement for the desired degree of condensation.

DESCRIPTION OF PREFERRED EMBODIMENTS

The amount of ammonia relative to β-chloroethylsilane or siloxane to be used depends upon the products desired. Generally speaking, the ammonia is used in at least a slight molar excess and preferably up to a 60 mole and greater excess. If only a slight molar excess of ammonia is employed there will be prepared a reaction product predominantly containing tris-(ethylsilyl)-amine wherein "x" is equal to 0. The greater the excess of ammonia is the greater will be the proportion of monoethylsilylamine (x equals 2) in the resultant reaction mixture. Since the hydrochloric or other hydrohalogen acid forming in the reaction mixture is bound by the ammonia that is charged into the reaction, a molar excess of halosilane to ammonia of at least 1:2 is generally required for the preparation of amino compounds. Generally speaking, the mole ratio of ammonia:-chlorosilane or chlorosiloxane is between 60 and 2:1, preferably between 30 and 10:1.

Since the yield of monoaminosilane increases as the excess of ammonia increases, an excess of 60 moles and more of ammonia per mole of chlorosilane can conveniently be used to obtain a reaction product in which the principle component is the monaminosilane.

Where the reactant is a chlorosiloxane the chlorosiloxane preferably has between 3 and 10 repeating units. The stoichiometry of the chlorosiloxane's reaction with the ammonia is analagous to the case where the reactant is a chlorosilane.

The reaction should be conducted at a temperature between 50° to 120° C. although it is contemplated to operate at higher temperatures if suitable pressure vessels are required. Generally speaking, the reaction is conducted at elevated pressures, especially at pressures of between 10 and 50 atmospheres. In practice the process is performed at the pressure resulting from the vapor pressure at the ammonia at the desired reaction temperature. Suitably an autogenous pressure can be employed.

The reaction is preferably performed in the absence of solvents although the use of inert solvents having a suitably high boiling point is also contemplated. Consideration must also be given, of course, to whether the solvent would react with the ammonia under the given reaction conditions. If it is desired to perform the reaction in the presence of a solvent an inert solvent should be employed, i.e., one which does not react with the ammonia for the use of an active solvent could absorb too much ammonia and effect the stoiciometry of the reaction.

The compounds prepared according to the present invention are suitable as adhesives to dressings for glass fiber impregnation or for incorporation into thermosetting resins, such as phenolic resins, for example, in order to achieve better adherence between these and inorganic oxidic materials.

These compounds can also be suitably employed as intermediates for the production of N-substituted aminoethylsilanes, which can also be used for the above-stated purposes.

In order to more fully illustrate the nature of the invention and the manner of practicing the same the following examples are presented.

EXAMPLES

EXAMPLE 1

In a pressure vessel of steel with a capacity of 1 liter, 0.5 mole of β-chloroethyltriethoxysilane and 25 moles of liquid ammonia were placed. The autoclave thus charged was then maintained for 12 hours at 70° C. After cooling, the excess ammonia was let off and the crude product was separated from the ammonium chloride. Vacuum distillation of the liquid at 5 Torr and a head temperature of 75° to 78° C. yielded a fraction consisting substantially of β-aminoethyltriethoxysilane (55 g).

The elemental analysis of the product was as follows:

|  | C | H | Si | N | Cl | Mol. Wt. |
|---|---|---|---|---|---|---|
| Calculated | 46.5 | 10.1 | 13.6 | 6.8 | — | 207 |
| Found | 46.8 | 10.3 | 13.7 | 7.0 | — | 209 |
| Index of refraction 20° C.: 1.4167 | | | | | | |
| Density 20° C./20° C.: 0.93 | | | | | | |

Another fraction followed which passed over at a pressure of 2 Torr and a head temperature of 125° C. (20 grams). It was identified as bis-(triethoxysilylethyl)-amine.

EXAMPLE 2

A mixture of 300 ml. of toluene, 0.5 mole of triethylamine and 0.5 mole of β-aminoethyltriethoxysilane, to which 0.5 g of ditertiarybutylparacresol had been added, was placed in a glass apparatus consisting of a 2-liter four-necked flask provided with reflux condenser, stirrer, dropping funnel and thermometer. At room temperature, 0.5 mole of methacrylic acid chloride was added drop by drop, with stirring. At the end of the addition of the metacrylic acid chloride, the reaction had ended. The precipitated triethylamine hydrochloride was filtered out, and after the addition of 2 g of ditertiarybutylparacresol to the filtrate, the latter was subjected to vacuum distillation. At 3 Torr and 128° C. a fraction is obtained which consisted of β-(methacrylato)-aminoethyltrialkoxysilane (109 g).

Elemental analysis of the product shows:

|  | C | H | Si | N | O | Bromine No. |
|---|---|---|---|---|---|---|
| Calculated | 52.4 | 9.1 | 10.2 | 5.1 | 23.2 | 58 |
| Found | 51.8 | 8.7 | 10.0 | 4.9 | — | 61 |

| | C | H | Si | N | O | Bromine No. |
|---|---|---|---|---|---|---|

Index of refraction 20° C.: 1.4509
Density 20° C./20° C.: 1.010

What is claimed is:

1. A compound which is an aminoethylsilane of the formula $$H_xN\text{-}[CH_2\text{-}CH_2\text{-}Si(OR'')_3]_{3-x}$$

or an aminoethylsiloxane have a structural unit $$[H_2N\text{-}CH_2\text{-}CH_2\text{-}Si\ O_{3/2}]$$

wherein R" is an alkyl, oxyalkyl or phenyl radical and x is 0, 1, or 2.

2. A compound according to claim 1 which is an aminoethylsilane.

3. A compound according to claim 1 which is an aminoethylsiloxane.

4. A compound according to claim 1 which is a β-aminoethyltriethoxysilane.

5. A compound according to claim 1 which is a bis-(triethyoxysilylethyl)-amine.

6. A process for preparing an aminoethylsilane or an aminoethylsiloxane which comprises contacting a β-halogenethylsilane of the formula $$Y\ (CH_2)_2\text{-}\underset{\underset{R'_a}{|}}{Si}\ (OR'')_{3-a}$$

or a siloxane with a repeating structural unit $$\left[Y\text{-}(CH_2)_2\text{-}\underset{\underset{R'_a}{|}}{Si}\ O_{\frac{3-a}{2}}\right]$$

wherein R" is an alkyl, oxyalkyl or phenyl radical, R' is a saturated or unsaturated aliphatic hydrocarbon radical, Y is a halogen atom, a is 0 or 1, with ammonia at a temperature of between 50° and 120° C.

7. A process according to claim 6 wherein the reactant is a β-halogenethylsilane.

8. A process according to claim 6 wherein the reactant is said siloxane.

9. A process according to claim 6 wherein a molar ratio of chlorosilane to ammonia of at least 1:2 is employed.

10. A process according to claim 9 wherein at least a 10 mole excess of ammonia is employed.

11. A process according to claim 6 wherein the process is conducted at an elevated pressure.

12. A process according to claim 11 wherein the pressure is that resulting from the vapor pressure of the ammonia at the reaction temperatures employed.

13. A process according to claim 6 carried out at a pressure of between 10 and 50 atmospheres.

14. A process according to claim 6 wherein the mol ratio of ammonia to β-halogenethylsilane or said siloxane is 2-60:1.

15. A process according to claim 6 wherein the mol ratio of ammonia to β-halogenethylsilane or said siloxane is 10-30:1.

16. A process according to claim 6 wherein there are 60 or more mols of ammonia per mol of β-halogenethylsilane or siloxane.

17. A process according to claim 13 wherein the mol ratio of ammonia to β-halogenethylsilane or siloxane is 10-30:1.

* * * * *